United States Patent
Hoppe et al.

(10) Patent No.: US 6,702,579 B1
(45) Date of Patent: Mar. 9, 2004

(54) ROOT CANAL INSTRUMENT AND METHOD FOR THE PRODUCTION THEREOF

(75) Inventors: Wolfgang Hoppe, Munster (DE); Edgar Schafer, Havixbeck (DE); Joachim Tepel, Münster (DE)

(73) Assignee: Gebruder Brasseler GmbH & Co. KG, Lemgo (DE)

( * ) Notice: Subject to any disclaimer, the term of this patent is extended or adjusted under 35 U.S.C. 154(b) by 0 days.

(21) Appl. No.: 09/856,217

(22) PCT Filed: Nov. 12, 1999

(86) PCT No.: PCT/EP99/08731

§ 371 (c)(1), (2), (4) Date: Sep. 10, 2001

(87) PCT Pub. No.: WO00/28915

PCT Pub. Date: May 25, 2000

(65) Prior Publication Data (65)

(30) Foreign Application Priority Data

Nov. 18, 1998 (DE) .......................... 198 52 931

(51) Int. Cl.⁷ .................................. A61C 5/02
(52) U.S. Cl. ...................................... 433/102
(58) Field of Search ......................... 433/102

(56) References Cited

U.S. PATENT DOCUMENTS 4,332,561 A   6/1982 McSpadden ............... 433/102
5,464,362 A   11/1995 Heath et al. ............... 433/102
5,752,825 A * 5/1998 Buchanan ................. 433/102

FOREIGN PATENT DOCUMENTS

DE     38 05 580 A1    8/1989
DE     197 23 695 C2   10/1998
SE         670756    *  7/1983

* cited by examiner

Primary Examiner—John J. Wilson
(74) Attorney, Agent, or Firm—Wolf, Greenfield & Sacks, P.C.

(57) ABSTRACT

In a dental root canal instrument which comprises a working part 1 provided with cutting edges, the working part being provided with one or more cutting edges 2 distributed around the circumference of the working part in the cross section thereof, and the instrument having a free end of the working part 1 designated as a tip 3, the tip 3 being formed as a rounded cap, and wherein a portion of the working part 1 which follows the tip 3 is designed over a length designated as a guide section 7 such that material is removed exclusively within a range of not more than 180° of the circumference thereof, the invention suggests that the working part 1 should comprise, as a rule, two or more helically extending cutting edges 2, with only one cutting edge 2 being arranged in the guide section 7 and the guide section 7 towards the tip being of a more tapering conicity than the remaining working part 1. As for the method, it is suggested that a cylinder should first be produced which is ground to obtain a blank, the blank being subjected in subsequent working steps to a deep-grinding process for forming the cutting edges 2.

13 Claims, 4 Drawing Sheets

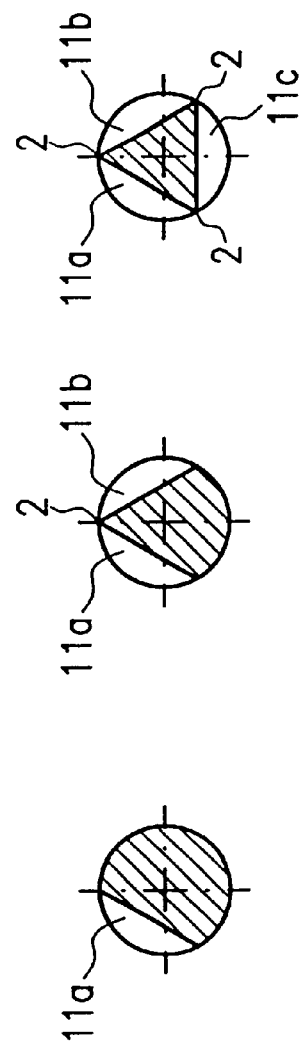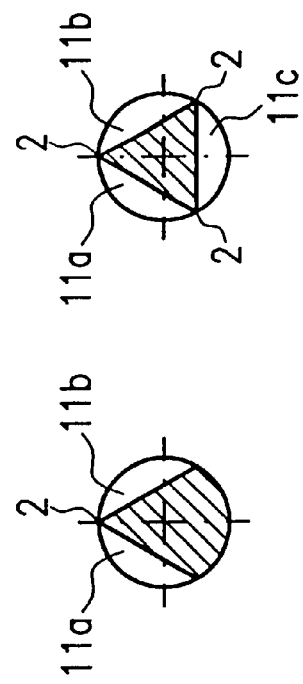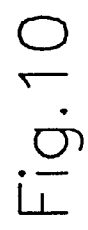

ROOT CANAL INSTRUMENT AND METHOD FOR THE PRODUCTION THEREOF

CROSS-REFERENCE TO RELATED APPLICATION

This application is the national stage under 35 U.S.C. §371 of International Application PCT/EP99/08731, filed Nov. 12, 1999, which claims foreign priority benefits under Title 35, United States Code, §119(a)–(d) and §365(b) of German Patent Application No. 19852931.7 filed Nov. 18, 1998.

BACKGROUND

1. Field of the Invention

The present invention relates to a dental root canal instrument according to the preamble of claim 1 and to a production method for a root canal instrument.

2. Related Art

The present invention relates to a dental root canal instrument according to the preamble of claim 1 and to a production method for a root canal instrument.

Such root canal instruments of a first type are known in practice as "reamers" or files. The working part of the generic root canal instruments is e.g. formed from a uniformly twisted rod having a triangular or tetragonal cross-section so that a cross section laid through the working part has three or four cutting edges distributed around the circumference of the instrument, the cutting edges extending up to the tip of the instrument.

Such generic instruments are used for cleaning infected root canals and to abrade material in the tooth root as evenly as possible around the circumference of the root canal. Since the portions of the tooth root adjacent to the root canal may be infected, it is desired that tooth material is removed, if possible, everywhere around the original free cross-section of the root canal.

Due to their inherent stiffness said generic root canal instruments remove not only more material on the outside of the bend of the root canal, but also have the drawback that in said area they exclusively treat the outer portion whereas there is no abrasion on the curve inside of said curved root canal area, so that foci of infection might be left there.

Said generic root canal instruments have cutting edge angles of less than 45°, i.e. the polygonal cross-sections are twisted such that the angle of the cutting edge relative to longitudinal axis of the root canal instrument is less than 45°. This results in an operation in which material is substantially removed in the root canal by rotating the instrument, with the instrument being advanced at the same time.

Generic root canal instruments of a second type are known as so-called "Hedström files". The working part of said files has a single coiled cutting edge so that only a single cutting edge can be seen on each cross-section laid through the working part. The cutting edge angle is here more than 45° and ranges from 45° to 90°. Consequently, this instrument entails an operation in which the instrument is moved back and forth in its longitudinal direction, as is known from the handling of files used in the wood- or metal-working industry.

With such an operation these root canal instruments of the second type do also not abrade material on the curved inside of the bent portion of the root canal and have the additional drawback that in comparison with the outer cross-sectional contour of the working area the inner core has a much smaller cross-section so that these instruments break easily when they are operated in rotating fashion in a way similar to that of the first-mentioned type of instrument.

DE 38 05 580 A1 discloses a tooth root-treating instrument whose tip is rounded to have a semispherical shape. As a consequence, there is no guide section. Furthermore, the two cutting edges extend into the tip portion.

U.S. Pat. No. 4,332,561 relates to a root canal instrument which comprises a semispherical tip which is followed by a small-diameter cylindrical attachment. Hence, the document does not show a guide section with only one cutting edge.

A further root canal instrument is already known from U.S. Pat. No. 5,464,362. The tip of said instrument is made conical like in the case of a drill; the tool comprises two cutting edges.

SUMMARY OF THE INVENTION

It is an object of the present invention to improve a generic root canal instrument such that it allows an operation that is as efficient as possible, i.e. a material removal that is an efficient as possible at the desired places of the root canal, and provides protection that is as high as possible against unintended material removal.

Furthermore, it is another object of the present invention to provide a method used for producing the root canal instrument of the invention, which while being very precise can be carried out easily and at low costs.

According to the invention a root canal instrument includes a working part which comprises three different portions: Firstly, the cap-like rounded and thus cutting edge-free tip of the working part ($1^{st}$ section), then the guide section ($2^{nd}$ section) which comprises a single cutting edge, namely exclusively over not more than 180° of its circumference, so that this cutting edge arrangement can achieve a very selective or targeted effect on the removing action with the root canal instrument and thus a very selective treatment of the canal wall on the inside of bends, and finally the section ($3^{rd}$ section) making up the largest part of the working part, in which the working part comprises two or more cutting edges and permits a correspondingly efficient action of removal. Since the cutting edges are designed to extend in helical fashion, a large machined space is created for receiving the removed material, whereby the efficiently of the root canal instrument is enhanced.

Since said third section of the working part accounts for the largest length of the working part, it can be said that the working part is "in principle" equipped with two or more cutting edges, but in contrast to said principle the guide section and the tip of the working part may be equipped, as already described, with only one cutting edge (in the guide section) or without any cutting edge (on the tip). Depending on the diameter of the working part, the guide section may have a very small length, i.e. in the case of small ISO sizes a length of about 1 mm. Nevertheless, the cutting edge arrangement on the guide section permits—even in the case of small lengths of said section—the desired guide action which makes it possible to exactly control a material removal on the inner wall of the curved portion of a root canal.

There may be provided an arrangement that is irregularly distributed around the circumference of the working part and comprises two or more cutting edges as a rule: For instance, cutting edges which are in relatively close vicinity with one another may have arranged diametrically opposite thereto a portion of the circumference of the working part without any cutting edge. The root canal instrument can rest with said cutting edge-free circumferential portion on a large area of the wall of the root canal and have a supporting effect which permits a particularly efficient removal work of the circumferentially opposite cutting edges on the wall of the root canal. Apart from this increased efficiency, such an arrangement of the cutting edges permits a reliable control of the material removal when material is just to be removed on a specific circumferential portion of the root canal.

When only two cutting edges are provided in principle, this will first of all result in a higher contact pressure for the two cutting edges, by comparison with the arrangement of several cuffing edges, and thus in an enhanced work performance and, secondly, depending on the design of the cross-sectional profile of the working part, in a very large machined space for receiving and possibly transporting away the removed material, whereby the efficiency of the cutting edges is further enhanced.

The arrangement of basically three cutting edges that are equally spaced apart from one another on the circumference of the working part may be chosen to achieve a practical and acceptable compromise when different, partly contradictory demands are to be met:

Firstly, the number of the cutting edges is sufficiently small for a high contact pressure of the cutting edges and thus for a high efficiency of the root canal instrument, secondly, the machined space is sufficiently large for transporting away the removed material, thereby enhancing the great efficiency of the root canal instrument, thirdly, the cross-sectional contour of the working part may be designed to be relatively sturdy, which increases the service life of the root channel instrument and its resistance to breakage, and thus reduces the risk of injury for the patient, and, fourthly, this arrangement permits an inexpensive production method for the working part in that said part can be made from a twisted rod material with a triangular or tetragonal cross-section.

The invention shall now be explained with reference to an embodiment regarding both the root canal instrument and the method, which embodiment is to be taken in conjunction with the drawings, in which:

BRIEF DESCRIPTION OF THE DRAWINGS

FIG. 5 is a perspective side view of an initial material for producing the root canal instrument;

FIG. 6 is a simplified side view of a blank for the root canal instrument according to the invention;

FIG. 8 is a sectional view through the working part, by analogy with the illustration of FIG. 7, after a first machining step;

FIG. 9 is a sectional view, similar to FIG. 8, after a second machining step;

FIG. 10 is a sectional view, similar to FIGS. 8 and 9, after a third machining step;

DETAILED DESCRIPTION

Figure 1:
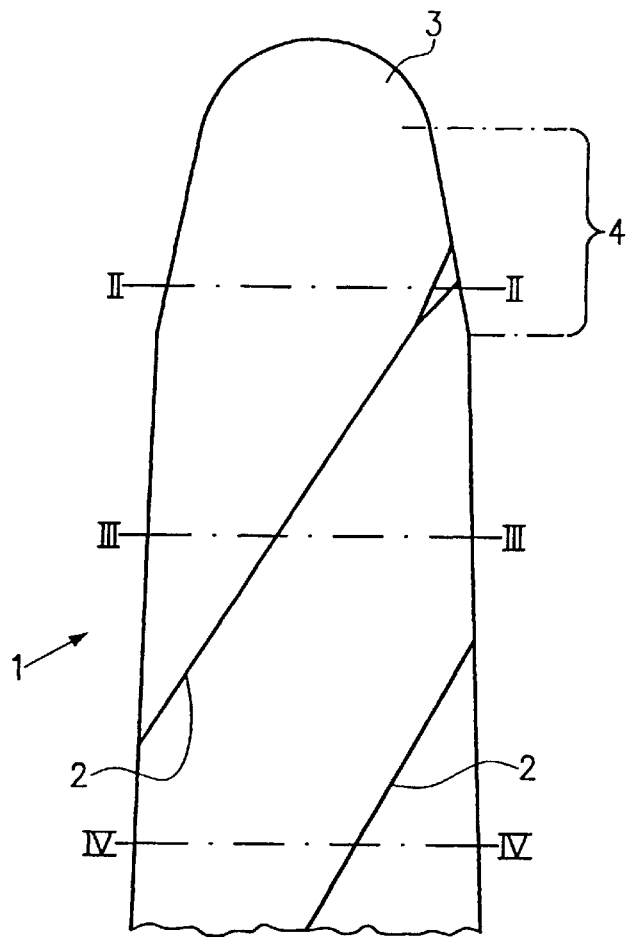
FIG. 1 is a purely schematic view on the portion of the tip and the portion of the working part of a root canal instrument near the tip.

In FIG. 1, reference numeral 1 generally designates the working part of a dental root canal instrument, said working part 1 being provided on its circumference with cutting edges 2 which extend around the working part 1 in helical fashion and are outlined in a purely schematic manner.

The free end of the working part 1 is designated as a "tip" 3, the term being adopted by tradition and the tip 3 being in fact not pointed, but rounded in the manner of a cap, e.g. in the form of a spherical segment.

The working part 1 is of a conicity which is made uniform over the major part of the length thereof. Next to the tip 3, however, the working part 1 comprises a transitional portion 4 of a much greater conicity. The transitional portion 4 is followed at the end of the transitional portion 4 remote from the tip 3 by a section of the working part 1 having a standard conicity.

Only one cutting edge 2 is arranged within the transitional portion 4 because said transitional portion 4 forms part of a guide section 7 in which the working part 1 is provided just over 180° of its circumferential surface with a single cutting edge 2. Due to the great conicity in the transitional portion 4, the cutting edge 2, which is per se sharp-edged, is slanted, as becomes apparent from FIG. 1 along sectional line II, but in particular from the cross-sectional view taken along said cross-sectional line II according to FIG. 2: As can be seen, only one cutting edge 2 is formed on the circumference, and said cutting edge 2 does not extend up to a sharp-pointed cutting edge, but is blunted because of the great conicity in the transitional portion 4.

The portion that is opposite to the cutting edge 2 is rounded in the manner of a circular segment, resulting in an abutment of a very large area for the root canal instrument on the wall of the root canal, so that thanks to said large abutment the efficiency of the single cutting edge 2 is enhanced and an undesired penetration of the root canal instrument into portions of the root canal wall that are not to be treated is efficiently prevented.

Figure 2:
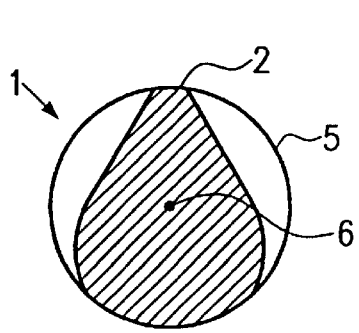
FIGS. 2–4 are cross-sections through the working part of FIG. 1 along the sectional planes marked by II–IV.
Figure 3:
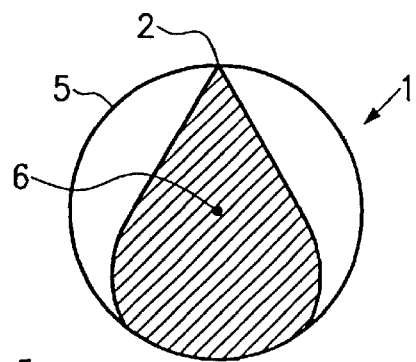

The transitional portion 4, which can be seen in FIG. 1, is followed by the further part of the guide section 7, a cross-section along sectional line III being visible in FIG. 3. The cutting edge 2, which has already been shown in FIG. 2, can here be seen with its sharp-edged operative tip, and it is here also apparent that only a single cutting edge 2 is formed on the circumferential portion of the working part 1 in the area of the guide section 7. In this instance, too, one obtains a large-area circumferential portion of the working part 1 that extends in rounded fashion and is opposite to the cutting edge 2, so that a large abutment will here also be created during the treatment of a root canal 8. The abutment exclusively effects a material removal in the area treated by the cutting edge 2, so that the dentist who is handling the root canal instrument can control in a very accurate manner on which circumferential portion of the root canal 8 such a material removal is to take place.

Furthermore, a very large machined space is created due to the single existing cutting edge 2, as becomes apparent from the circular line 5 shown in FIGS. 2 and 3: This circular line 5 describes the circle around a center point 6 of the working part 1 within which the cross section of the working part 1 is arranged such that said circular line 5 corresponds approximately to the lumen of the root canal 8 which is filled by the working part 1. The large machined space which has been provided makes it possible to receive and optionally discharge the removed material in a reliable manner, so that the root canal instrument does not become clogged and does not lose its efficiency. In particular, this large and free machined space is created in that the cross-section of the working part is obtained from a basically triangular contour of the rod material forming the working part 1.

Figure 4:
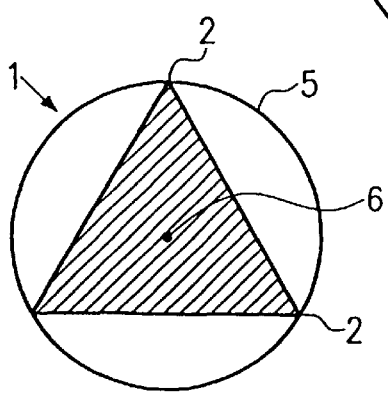

As can be seen in FIG. 4, a cross section is obtained according to sectional line IV in FIG. 1 through the longest section of the working part 1 that is positioned between the guide section and the handling part (not shown) of the root canal instrument. This handling part may be designed as a grip or handle or as a connection part that is connectable to a treating machine. In this largest section of the working part 1 the latter has a triangular cross-section on three cutting edges 2 that are uniformly offset on the circumference thereof, with the circular line 5 shown in FIG. 5 representing—due to the helically coiled cutting edges 2—the outer circumferential contour of the working part 1 in said largest section of its length. The conicity of the working part 1 becomes apparent from the different diameters of the circular lines 5 in FIGS. 2 to 4.

Each of FIGS. 5 to 11 shows individual working sections for producing the root canal instrument according to the invention.

First of all, FIG. 5 schematically shows an initial material which is shaped in the form of a cylinder that may e.g. have a length of 50 mm. It is made from a rod or a ring consisting either of a stainless spring steel or of a nickel-titanium alloy. It can be produced in a forming process or in a machining process, e.g. by way of grinding.

In a subsequent working step (see FIG. 6), a blank is made. The tip 3 of the blank is first of all frustoconically ground and then rounded off, as has been explained in the preceding description. Furthermore, the blank is frustoconically ground by analogy with the above information, wherein both the conical shape of the transitional portion 4 and that of the guide section 7 (see FIG. 1) are formed. Thus both the length and the respective conical angle of the conical portion correspond to the dimensions of the finished root canal instrument.

Figure 7:
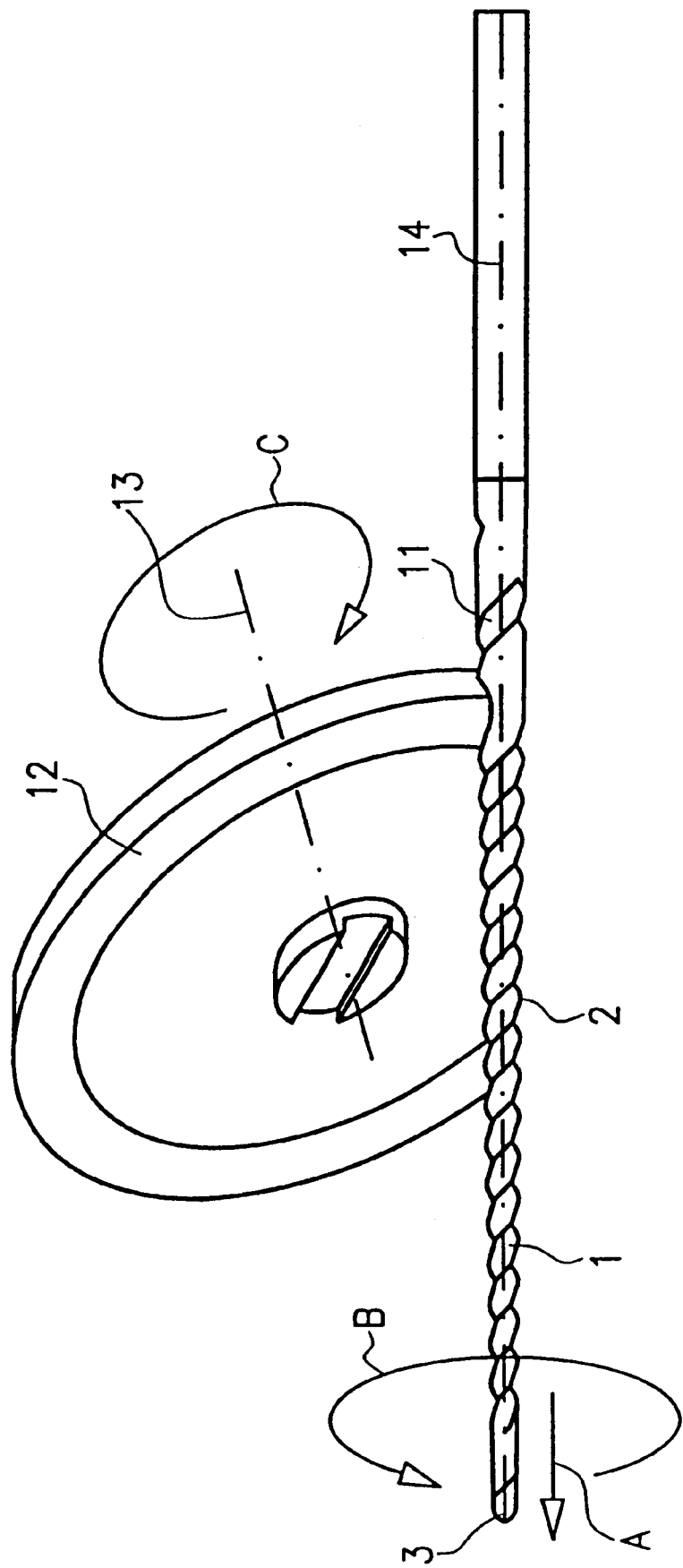
FIG. 7 is a simplified illustration of the machining operation for producing the root canal instrument according to the invention.

FIG. 7 schematically shows the preparation of the spiral-like cutting edges 2 and grooves 11. They are produced by means of a rotatably supported grinding wheel 12 in a special deep-grinding process. The previously conically ground portion (see FIG. 6), which has a circular cross-section, is guided along the rotating grinding wheel 12 while the blank is rotated around its own longitudinal axis. The rotational movement of the blank is illustrated by arrow B whereas the longitudinal movement is indicated by arrow A. Arrow C shows the rotation of the grinding wheel around its stationary shaft 12. Thus a first groove 11 that extends in spiral-like fashion around the axis 14 is formed according to the invention.

FIG. 8 is a sectional view showing this machining operation. It goes without saying that said machining operation can be carried out either in one pass or in several successive and analogous passes. Thus a groove 11 or area which extends in spiral-like fashion around the instrument axis 14 (FIG. 8) is formed and extends over the whole length of the conical portion.

Following this machining operation the blank is indexed. This means that the position of the produced groove 11 is exactly determined and the blank is aligned therewith. Subsequently, the blank is again moved along the grinding wheel 12, whereby a second groove 11 is produced. Said groove is shown in section in FIG. 9, with the first groove being marked as 11a and the second groove as 11b. It also goes without saying that said machining operation can be carried out by the grinding wheel 12 either in one pass or in several passes.

As follows in particular from the illustration of FIG. 9, a cutting edge 2 is formed between the two grooves 11a and 11b.

FIG. 10 shows that when the last operation is repeated once again a third groove 11c can be formed for producing two further cutting edges 2. However, it is also within the scope of the present invention to give the root canal instrument a tetragonal or pentagonal or any other desired polygonal cross-sectional shape.

Figure 11:
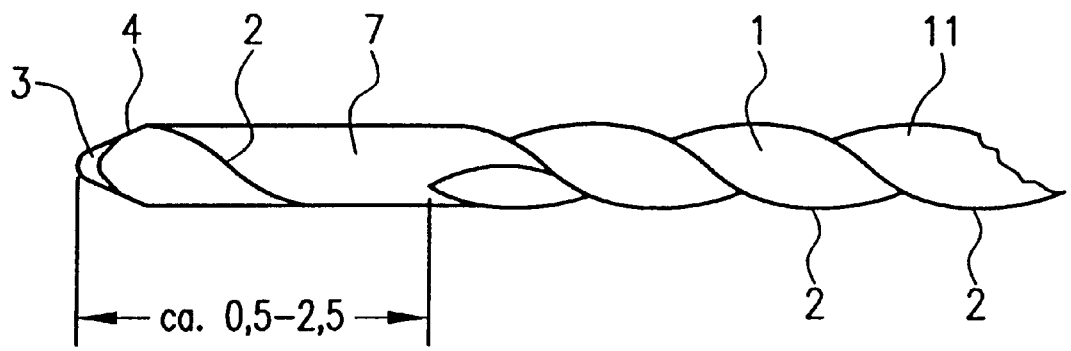
FIG. 11 is an enlarged, schematic illustration of the tip of the root canal instrument shown in FIG. 7.
Figure 12:
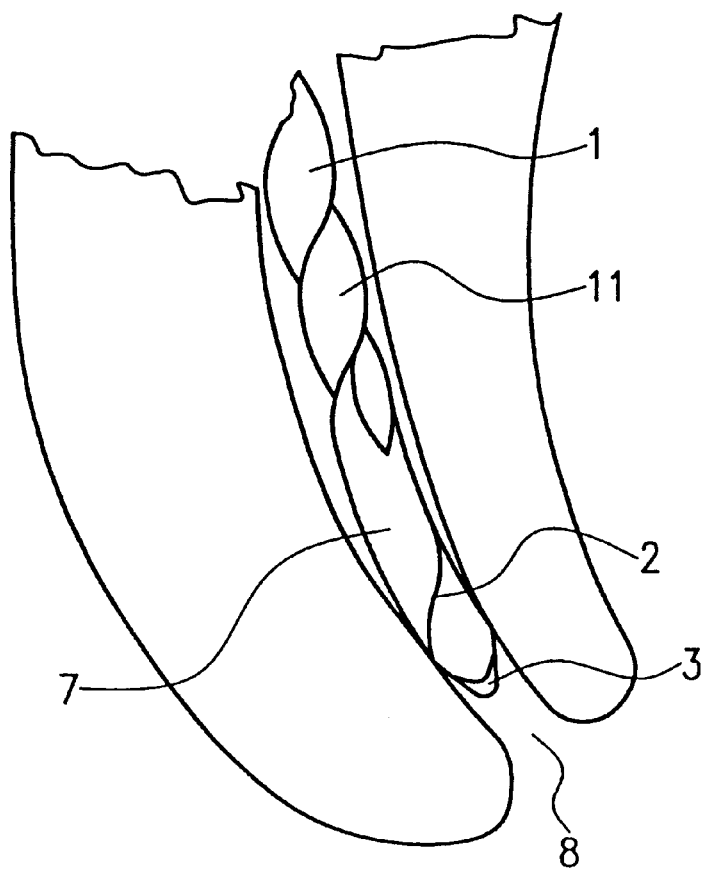
FIG. 12 is a simplified sectional view of a tooth root with a root canal in which the root canal instrument of the invention is used.

When the second and/or the further spiral grooves 11 are ground, a length of about 1 mm first remains untreated in the front part of the blank, as can be seen in FIG. 11, before the grinding wheel 12 dips into the area of the blank. This has the effect that the triangular or polygonal cross-sectional shape of the root canal instrument is only given its complete form after a length of about 1 mm. In the close vicinity of the tip 3 of the root canal instrument a guide section is thereby created that has a length of about 0.5 to 2.5 mm and does not remove material at the one side, but removes material at the other side, thereby ensuring a reliable treatment of curved root canals 8. The cross-sectional shape shown in FIG. 9 is e.g. of a design in the case of which only one cutting edge 2 is provided for and is opposite to a rounded portion. Said rounded portion serves as a support whereas the cutting edge 2 carries out the treatment.

It is within the scope of the method of the invention that a metal-bonded grinding wheel with a CBN grinding grain is preferably used for grinding the blank, provided that the blank is made from a stainless high-quality steel or spring steel. When the blank is made from a nickel-titanium alloy, a resin-bonded grinding wheel with a diamond-based grinding grain is preferably used. The grain sizes of the grinding wheels are preferably between 46 and 76 $\mu$m.

Particularly advantageous machining parameters are given according to the invention whenever a cutting speed of 27 m/sec and a feed rate of 0.04 m/min are employed in the case of a blank made from stainless steel. In a blank made from a nickel-titanium alloy it is of particular advantage when the cutting speed is 45 m/sec and the feed rate 0.08 m/min.

It goes without saying that the illustrations in FIGS. 2 to 4 correspond to those of FIGS. 8 to 10. In FIGS. 8 to 10 the rounded portions relative to the untreated circumferential portions of the blank as well as the exact design of the cutting edge (see FIG. 2) are not shown in detail. Thus FIGS. 8 to 10 serve in particular a better understanding of the invention while FIGS. 2 to 4 are more exact illustrations of the respective cross-sections in the finished state. The rounded portions as shown serve, in particular, the purpose of deburring and an improved handling of the root canal instrument.

The present invention is not limited to the embodiments shown; rather many modifications and alterations are possible within the scope of the present invention.

What is claimed is:

1. A root canal instrument comprises: a working part provided with cutting edges, said working part being provided with a plurality of cutting edges distributed over the circumference thereof on the cross section thereof; and said instrument having a free end of said working part designated as a tip, said tip being designed as a rounded cap, and a transitional portion of said working part which follows said tip being designed over a length designated as a guide section such that material is removed exclusively within a range of not more than 180° of the circumference thereof, said working part comprising two or more helically extending Cutting edges, only one cutting edge being arranged in said guide section and said guide section towards said tip being of a more tapering conicity than the remaining working part.

2. The root canal instrument according to claim 1, wherein two or more cutting edges are irregularly spaced apart from one another on the circumference of said working part.

3. The root canal instrument according to claim 1 or 2, wherein said working part comprises two cutting edges on its circumference.

4. The root canal instrument according to claim 1 or 2, wherein said working part is provided on its circumference with three cutting edges that are evenly spaced apart from one another.

5. A method for producing a root canal instrument which comprises a working part which is provided with two or more helically extending Cutting edges and which is followed by a guide section including only one cutting edge, which towards a tip of said root canal instrument is of a more tapering conicity than the remaining working part, said guide section being designed to remove material exclusively within a range of not more than 180° of the circumference thereof, producing a cylinder from an initial material, grinding on said cylinder a tip and a frustoconical portion next to said tip, said frustoconical portion having the above-described different conical shapes, rotating and grinding said cylinder with said frustoconical portion around its longitudinal axis by means of a rotating grinding wheel which is movable along said cylinder with said frustoconical portion, so as to form a groove, indexing said cylinder with said frustoconical portion and grinding a rotating grinding wheel along said cylinder with said frustoconical portion so as to form a further groove.

6. The method according to claim 5, wherein said grinding operation is repeated several times.

7. The method according to any one of claim 5 or 6, further wherein the last groove is ground a length of about 0.5 to 2.5 mm is depending upon the ISO size of the instrument in the front guide section that is subsequent to said tip and does not effect a material removal at the one side, but removes material at the other side, thereby ensuring a reliable treatment of curved root canals, said length being not machined by said grinding wheel.

8. The method according to claim 7, wherein in the part having a length of about 0.5 to 2.5 mm a guide section is formed which does not remove material at the one side, but removes material at the other side, thereby ensuring a reliable treatment of curved root canals.

9. The method according to any one of claims 5 to 6, characterized in that a metal-bonded grinding wheel with a CBN grinding grain is used for grinding said grooves.

10. The method according to any one of claims 5 to 6, wherein a resin-bonded grinding wheel with a diamond-based grinding grain is used for grinding said grooves.

11. The method according to any one of claims 5 to 6, wherein a grinding wheel having a grain size between 46 and 76 μm is used for grinding said grooves.

12. The method according to any one of claims 5 to 6, wherein for the production of a root canal instrument made from stainless steel a cutting speed of 27 m/sec and a feed rate of 0.04 m/min are employed for forming said grooves and said cutting edges, respectively.

13. The method according to any one of claims 5 to 6, wherein for the production of a root canal instrument made from a nickel-titanium alloy a cutting speed of 45 m/sec and a feed rate of 0.08 m/min are employed for forming said grooves and said cutting edges, respectively.

* * * * *